| United States Patent [19] | [11] Patent Number: 5,025,106 |
|---|---|
| Cook | [45] Date of Patent: Jun. 18, 1991 |

[54] PREPARATION OF AQUEOUS SOLUTIONS OF ACETOACETAMIDE

[75] Inventor: Steven L. Cook, Kingsport, Tenn.

[73] Assignee: Eastman Kodak Company, Rochester, N.Y.

[21] Appl. No.: 600,648

[22] Filed: Oct. 22, 1990

[51] Int. Cl.$^5$ .......................................... C07C 233/05
[52] U.S. Cl. .......................................... 564/199; 564/4
[58] Field of Search .................................... 564/199, 4

[56] References Cited

U.S. PATENT DOCUMENTS

| 2,152,132 | 3/1939 | Boese | 544/176 |
|---|---|---|---|
| 3,694,431 | 9/1972 | Fuchs et al. | 564/199 |
| 4,129,596 | 12/1978 | Künstle et al. | 564/199 |
| 4,571,433 | 2/1986 | Künstle et al. | 564/4 |

FOREIGN PATENT DOCUMENTS

| 3101650 | 8/1982 | Fed. Rep. of Germany | 564/199 |
|---|---|---|---|
| 0131951 | 8/1983 | Japan | 564/199 |
| 0828423 | 2/1960 | United Kingdom | 564/199 |
| 0858529 | 1/1961 | United Kingdom | 564/199 |

*Primary Examiner*—Glennon H. Hollrah
*Attorney, Agent, or Firm*—J. Frederick Thomsen; William P. Heath, Jr.

[57] ABSTRACT

Disclosed is a process for the preparation of aqueous solutions of acetoacetamide wherein diketene and aqueous ammonia having an ammonia concentration of about 6.0 to 9.0 weight percent are continuously fed to a reaction zone at rates which maintain in the reaction zone a pH of about 7.0 to 8.2 and a residence time of about 20 to 150 minutes while (i) maintaining the temperature of the reaction zone at about 40° to 75° C. and (ii) subjecting the contents of the reaction zone to vigorous agitation. An aqueous product solution having an acetoacetamide concentration of about 25 to 35 weight percent is continuously removed from the reaction zone.

4 Claims, No Drawings

PREPARATION OF AQUEOUS SOLUTIONS OF ACETOACETAMIDE

This invention pertains to a novel process for the preparation of aqueous solutions of acetoacetamide. More particularly, this invention pertains to the continuous preparation of stable, aqueous solutions of acetoacet. amide which avoids the necessity of adjusting the pH of aqueous acetoacetamide solution formed by the reaction of aqueous ammonia with diketene.

The state of the art pertaining to the manufacture of aqueous solutions of acetoacetamide is described in U.S. Pat. No. 4,571,433. This patent discloses the preparation of stable solutions of acetoacetamide by first reacting diketene with an excess of aqueous ammonia and then immediately adding to the aqueous solution thus obtained a sufficient amount of diketene with vigorous agitation to obtain a pH of 6-7, preferably 6.5. According to the patent, the pH adjustment counteracts the tendency of the acetoacetamide to decompose and/or form by-products by further reaction and also maintains the purity of the stabilized solution by suppressing the formation of salt-like products and derivatives of $\beta$-aminocrotonic acid amide.

European Patent Application 59,792 discloses a similar process wherein an acid such as acetic acid is added to an aqueous solution of acetoacetamide formed by the reaction of diketene and aqueous ammonia at a pH of 8 to 10 to adjust the pH of the acetoacetamide solution to 6 to 7.5. The disadvantages resulting from the use of this stabilization method are described in the U.S. patent cited above.

The means described in the above patents for obtaining stabilized, aqueous solutions of acetoacetamide are difficult to use in commercial operations, particularly in the manufacture of aqueous acetoacetamide solutions by a continuous process. In addition to the problem of acetoacetamide decomposition, I have found that aqueous solutions of acetoacetamide prepared by the reaction of diketene with aqueous ammonia can generate a gas which results in a build-up of pressure when the acetoacetamide solution is packaged in sealed containers such as drums. Such a pressure build-up constitutes a hazard which virtually prohibits the packaging and shipment of acetoacetamide solutions according to procedures and practices typically employed in the chemical industry. Normally, a pressure build-up of approximately 5 pounds per square inch gauge (psig) can cause steel drums containing an acetoacetamide solution to rupture, thereby presenting a hazardous condition which precludes storage of such solutions in sealed containers. Another problem I have found is the formation of a solid (insoluble) material, either during the preparation of the acetoacetamide solution or upon storage of it. Although the presence of such solids in aqueous acetoacetamide solutions does not necessarily limit the utility of the acetoacetamide solution, it does decrease the assay (purity) of the acetoacetamide and is an undesirable characteristic which can affect the value of the solution product.

I have discovered that stable, aqueous solutions of acetoacetamide may be prepared by a continuous process wherein diketene and aqueous ammonia are contacted with vigorous agitation under carefully controlled conditions. The acetoacetamide solutions thus obtained normally do not contain any detectable amount of 3-amino-2-butenamide ($\beta$-aminocrotonic acid amide) or derivatives thereof and, when packaged in sealed containers, do not cause any significant pressure build-up upon storage over a prolonged period of time.

The process provided by the present invention comprises the continuous preparation of an aqueous solution of acetoacetamide by (1) continuously feeding to a reaction zone diketene and aqueous ammonia having an ammonia concentration of about 7.0 to 8.0 weight percent at rates which maintain in the reaction zone a pH of about 7.0 to 8.0 and a residence time of about 20 to 150 minutes while (i) maintaining the temperature of the reaction zone at about 40° to 75° C. and (ii) subjecting the contents of the reaction zone to vigorous agitation and (2) continuously removing from the reaction zone an aqueous product solution having an acetoacetamide concentration of about 25 to 35 weight percent.

The acetoacetamide solutions which may be obtained in accordance with my novel process have excellent purity and stability. The solutions do not contain any significant amount of 3-amino-2-butenamide or derivatives, e.g. typically not more than about 500 ppm, based on the weight of the solution, of such impurities. The excellent stability is manifested by only a minor decrease in acetoacetamide concentration, the formation of little, if any, solid materials and, most importantly, the absence of significant gas formation, upon storage, e.g., storage over a period of 30 to 90 days. For example, the acetoacetamide content of the aqueous solutions of acetoacetamide obtained in accordance with my invention normally does not decrease by more than about 1 percent of the initial weight concentration upon storage for 30 days at ambient conditions. Furthermore, the aqueous acetoacetamide solutions obtained by means of my process contains less than about 500 ppm, based on the weight of the solution, and preferably no, insoluble material and does not cause a significant pressure build-up when packaged in sealed containers. The "significant pressure build-up" may be defined as a pressure of 10 psig or greater generated within a sealed container having at least 50 percent of its volume filled with aqueous acetoacetamide solution.

In the practice of the process, diketene and aqueous ammonia solution having an ammonia concentration in the range of about 6 to 9, preferably about 7 to 8, weight percent are continuously fed to, and aqueous acetoacetamide is continuously removed from, a reactor provided with cooling means to maintain the contents thereof at a temperature of about 40° to 75° C. The capacity of the reactor is sufficient to provide a residence time of about 20 to 150 minutes, preferably about 60 to 120 minutes, relative to the materials fed. Generally, shorter residence times require the use of higher temperatures to achieve the advantages of the present invention. The average volume ratio of diketene to aqueous ammonia fed is in the range of about 1:3 to 1:4, depending on the concentration of the ammonia solution fed. The feed ratio is controlled to maintain a pH of about 7.0 to 8.2, preferably about 7.3 to 8.0, in the reactor. In a preferred embodiment of the invention, the diketene feed is maintained at a substantially constant value which provides the required residence time. The pH of the reaction mixture is maintained within the range specified by providing means to detect the pH of the reactor contents and means for regulating the aqueous ammonia feed which are responsive to the pH detecting means.

The acetoacetamide concentration of the product solution continuously removed from the reactor is about 25 to 35, preferably 28 to 32, weight percent, based on the weight of the solution. The reactor is equipped with means for providing vigorous agitation of the reaction mixture. Such agitation may be provided with any device equipped with a suitable mixing blade which operates at high revolutions.

When my novel process is practiced within the most preferred combination of process parameters and conditions, i.e., a pH of about 7.8, a temperature of about 45° to 55° C., and a residence time of about 70 to 120 minutes using 7.3 to 7.9 weight percent aqueous ammonia, the product solution has an acetoacetamide concentration of about 30 weight percent, a color of 100 as determined by platinum-cobalt scale color measurement, contains no solid material and does not develop pressure after prolonged storage in a sealed container, and the pH of the solution stabilizes at a value of about 7.0. The acetoacetamide concentration of the product solution decrease by only approximately 1% over a two-month storage time at ambient temperature (25° C.) which compares favorably to the burdensome stabilization procedures described in the prior art. The acetoacetamide concentration and pH of a typical aqueous acetoacetamide solution prepared by means of the particularly preferred process parameters and conditions described above and stored for 70 days are shown below.

| Days | Acetoacetamide Concentration | pH |
|---|---|---|
| 0 | 29.99 | 7.6 |
| 7 | 29.73 | 7.2 |
| 14 | 29.51 | 7.0 |
| 28 | 29.14 | 7.0 |
| 42 | 28.94 | 7.0 |
| 56 | 28.79 | 7.0 |
| 70 | 28.90 | 7.0 |

Attempts to prepare aqueous acetoacetamide solutions according to the parameters and conditions described herein but using more concentrated ammonia solutions, e.g., up to 9.8 weight percent, results in product solutions which contain solid material and/or cause an unacceptable pressure build-up when stored in sealed containers. Attempts to compensate for these problems by raising the reaction pH eventually leads to a drop in acetoacetamide concentration toward the 30 weight percent value obtained by the use of the aqueous ammonia solutions according to the present invention.

The process of the present invention is further illustrated by the following examples. The apparatus used consisted of a glass reactor having a working volume of 200 mL and equipped with inlets for feeding the diketene and aqueous ammonia reactants, an outlet for removing the aqueous acetoacetamide product, a water jacket for cooling the reactor and a mixer operated at 5000 revolutions per minute to provide vigorous agitation. A temperature sensor in the reaction chamber thermowell is connected to a controller which opens and closes a solenoid water valve to admit cooling water to the water jacket as required to maintain the reaction mixture at the temperature selected. A calibrated pH probe is immersed in the reaction mixture contained in the reactor and is connected to a controller which regulates the flow of the aqueous ammonia to the reactor. The diketene feed is set at a constant value as determined by the residence time desired. The acetoacetamide product solution is removed, i.e., overflowed, through an outlet located in the upper portion of the reactor. Although various analytical techniques may be used to determine the assay (concentration) of the acetoacetamide of the product solution, the preferred method utilizes a potentiometric titration of the active methylene group with tetrabutyl ammonium hydroxide. The color values given are determined by comparisons with color standards on the platinum-cobalt scale.

EXAMPLES 1-3

The process is carried out using 7.5 weight percent aqueous ammonia, a temperature of 50° C., a residence time of 75 minutes and a pH of 7.1 (Example 1), 7.3 (Example 2) or 7.5 (Example 3). The product solutions produced at each pH have acetoacetamide concentrations of 29-30 weight percent and a color value of 90-110. A sample of each product solution is placed in a 120 mL, thickwalled, glass tube and sealed with a sealing head fitted with a pressure gauge. After a period of 30 days, no pressure build-up is observed for any of the three product solutions.

Repeating this procedure using a pH of 7.3 and a residence time of 120 minutes, gives a product solution having the same characteristics but having a color value of 150.

EXAMPLE 4

The procedure described in Examples 1-3 is repeated at a pH of 7.1, a temperature of 70° C. and a residence time of 20 minutes. The product solution obtained does not contain any solid material, has a color value of 100 and does not develop any pressure when stored for 4 days in the sealed tube described above. The use of lower temperatures in combination with the 20 minute residence time tends to result in the formation of a product solution which contains solids and causes a pressure build-up within 4 days of storage.

EXAMPLE 5

The procedure described in Examples 1-3 is repeated at a pH of 7.1, a temperature of 40° C. and a residence time of 150 minutes. The product solution obtained contains a minor amount of solid material but does not develop any pressure when stored in the sealed tube described above.

COMPARATIVE EXAMPLE 1

The procedure of Examples 1-3 is repeated at a pH of 6.5 and a temperature of 70° C. using a residence time of 40 minutes and 22 weight percent aqueous ammonia. The product solutions contained 58.6 weight percent acetoacetamide and 0.25 weight percent solid material. A sample of the product solution is evaluated for the development of pressure as described above. After 30 day storage period, the pressure increases from 0 to 12 psig.

COMPARATIVE EXAMPLE 2

The procedure of Comparative Example 1 is repeated except that 7.5 weight percent aqueous ammonia and a residence time of 20 minutes are used. The product solution contains 32.5 weight percent acetoacetamide and 0.1 weight percent or less solid material. A sample (74 mL, 80 g) of the product solution is placed in the above-described pressure-testing tube and found to develop a pressure of 12 psig over a 14 day period.

COMPARATIVE EXAMPLE 3

The procedure of Examples 1-3 is repeated at a pH of 8.5 and a temperature of 50° C. using a residence time of 120 minutes. The product solution is satisfactory relative to solid material and pressure build-up but has an unacceptably low concentration (24 weight percent) of acetoacetamide.

COMPARATIVE EXAMPLE 4

The procedure of Examples 1-3 is repeated at a pH of 7.8 and a temperature of 50° C. using a residence time of 75 minutes and 9.8 weight percent aqueous ammonia. The product solution contains 35.5 weight percent acetoacetamide and solid material and causes a pressure build-up.

COMPARATIVE EXAMPLE 5

The procedure of Comparative Example 4 is repeated at a pH of 8.2. The product solution has an acetoacetamide concentration of 33 8 weight percent and a color value of 100. However, the solution did cause an unacceptable build-up of pressure when stored in a sealed container as described above.

The process described herein may be advantageously employed in the manufacture of N-substituted acetoacetamides as well as unsubstituted acetoacetamide. Thus, primary amines such as methylamine and arylamines and secondary amines such as dimethylamine and diethylamine may be reacted continuously with diketene according to the process parameters and conditions disclosed above to obtain N-methyl-, N-aryl-, N,N-dimethyl- and N,N-diethylacetoacetamides.

The invention has been described in detail with reference to preferred embodiments thereof. However, variations and modifications of the invention may be made within the spirit and scope of the invention.

I claim:

1. Process for the continuous preparation of an aqueous solution of acetoacetamide which comprises the steps of (1) continuously feeding to a reaction zone diketene and aqueous ammonia having an ammonia concentration of about 6.0° to 9.0 weight percent at rates which maintain in the reaction zone a pH of about 7.0° to 8.2 and a residence time of about 20 to 150 minutes while (i) maintaining the temperature of the reaction zone at about 40° to 75° C. and (ii) subjecting the contents of the reaction zone to vigorous agitation and (2) continuously removing from the reaction zone an aqueous product solution having an acetoacetamide concentration of about 25 to 35 weight percent.

2. Process according to claim 1 wherein the temperature is about 40° to 60° C. and the residence time is about 60 to 120 minutes.

3. Process according to claim 1 for the continuous preparation of an aqueous solution of acetoacetamide which comprises the steps of (1) continuously feeding to a reaction zone diketene and aqueous ammonia having an ammonia concentration of about 7.0 to 8.0 weight percent at rates which maintain in the reaction zone a pH of about 7.3 to 8.0 and a residence time of about 60 to 120 minutes while (i) maintaining the temperature of the reaction zone at about 40° to 60° C. and (ii) subjecting the contents of the reaction zone to vigorous agitation and (2) continuously removing from the reaction zone an aqueous product solution having an acetoacetamide concentration of about 25 to 35 weight percent.

4. Process for the continuous preparation of an aqueous solution of acetoacetamide which comprises the steps of (1) continuously feeding to a reaction zone diketene and aqueous ammonia having an ammonia concentration of about 7.0 to 8.0 weight percent at rates which maintain in the reaction zone a pH of about 7.3 to 7.9 and a residence time of about 70 to 120 minutes while (i) maintaining the temperature of the reaction zone at about 45° to 55° C. and (ii) subjecting the contents of the reaction zone to vigorous agitation and (2) continuously removing from the reaction zone an aqueous product solution having an acetoacetamide concentration of about 25 to 35 weight percent.

* * * * *